United States Patent [19]

LeBoeuf

[11] 4,330,402
[45] May 18, 1982

[54] WATER SAMPLING AND DISPOSAL APPARATUS FOR AN OFFSHORE OPERATING SITE

[75] Inventor: Harry P. LeBoeuf, Morgan City, La.

[73] Assignee: Texaco Inc., White Plains, N.Y.

[21] Appl. No.: 195,556

[22] Filed: Oct. 9, 1980

[51] Int. Cl.³ .............................................. E02B 3/20
[52] U.S. Cl. .............................. 210/170; 166/105.1; 417/401
[58] Field of Search ........................................ 210/170; 166/105.1-105.5; 60/329, 325; 417/237, 401

[56] References Cited

U.S. PATENT DOCUMENTS

| | | | |
|---|---|---|---|
| 3,159,105 | 12/1964 | Chenault | 417/401 |
| 3,216,651 | 11/1965 | King et al. | 417/401 |
| 3,420,183 | 1/1969 | Hart | 166/105.1 |
| 3,761,204 | 9/1973 | Pauliukonis | 417/401 |
| 3,839,863 | 10/1974 | Frazier | 417/401 |
| 4,198,300 | 4/1980 | Williams | 210/170 |

FOREIGN PATENT DOCUMENTS 1215760 12/1970 United Kingdom ................ 417/401

Primary Examiner—Theodore A. Granger
Attorney, Agent, or Firm—Carl G. Ries; Robert A. Kulason; Robert B. Burns

[57] ABSTRACT

Apparatus for sampling and disposing of water which has been separated from a water polluting element, the latter being lighter than the water. The apparatus includes an elongated upright caisson or pile which is disposed in a body of water, and which is adapted to contain a quantity of the water as well as the pollutant element. A submerged sampling apparatus is positioned at the lower end of the caisson and is actuated by gas pressure controlled from the water's surface to periodically withdraw a measured sample of the pollutant free water to assure its purity.

4 Claims, 2 Drawing Figures

WATER SAMPLING AND DISPOSAL APPARATUS FOR AN OFFSHORE OPERATING SITE

BACKGROUND OF THE INVENTION

In offshore operations, as for example offshore well drilling and producing of petroleum products from a fixed structure, a considerable quantity of water is normally withdrawn from the earth during the producing operation. The water is generally intermixed with, or in suspension with crude oil, gas, or other liquids even though not forming a solution therewith.

Thus, during the initial processing of the produced product such as crude oil, it is necessary to dispose of the water. The most practical outlet for such disposal would be merely to discharge it overboard from the offshore structure. Normally however, the water is treated prior to such discharge to remove as much as possible of the matter contained therein which would tend to pollute the surrounding environment.

In accordance with the instant invention, means is provided to avoid any possible environmental degradation resulting from the discharge of materials into the surrounding body of water. This is achieved by depositing the polluted water in its entirety into a pile or caisson which is so constructed to contain the discharged matter. The lighter, nondissolved elements such as petroleum based segments will surface to the top of the caisson. The pollutant free water will then gravitate toward the pile lower end, thence pass freely into the surrounding body of water.

To assure that this pollutant free water is sufficiently clean to be passed into the surroundings, its quality is monitored on a continuous basis. This necessity often stems from governmental regulations that prohibit the discharge of any materials which contain petroleum products, into the surrounding water.

To assure the integrity of the discharge system, the herein disclosed sampling means is utilized for withdrawing specimens of the treated water prior to the latter being discharged from the pile. Further, the withdrawal is achieved by utilizing process gas as the driving medium for the withdrawal pump.

Toward facilitating the sampling operation, the instant apparatus permits a predetermined, set amount of water to be withdrawn from the disposal pile lower end. This withdrawal follows either a systematic sampling schedule, or a substantially continuous process. Thus, discrete water samples are withdrawn from a point preferably adjacent to the pile lower end where the water leaves the pile.

The sampling apparatus includes a gas powered prime mover which is communicated with a source of process gas at the water's surface. Operationally, the apparatus effectuates the ingestion of a set quantity of water to be sampled. The sample is then forced from the lower end of the pile, upwardly to a sampling station where it is withdrawn and submitted for analysis to determine its purity.

The sampling pump or prime mover is communicated with a source of compressed gas at, and controlled from the water's surface. Preferably this source comprises a supply of pressurized gas which has been extracted or separated as a result of the petroleum producing process.

It is therefore an object of the invention to provide a method to assure the integrity of discharged water at an offshore operating site. A further object is to provide means for continuously sampling a pool of water which is to be discharged into the surrounding water at an offshore site.

Figure 1:
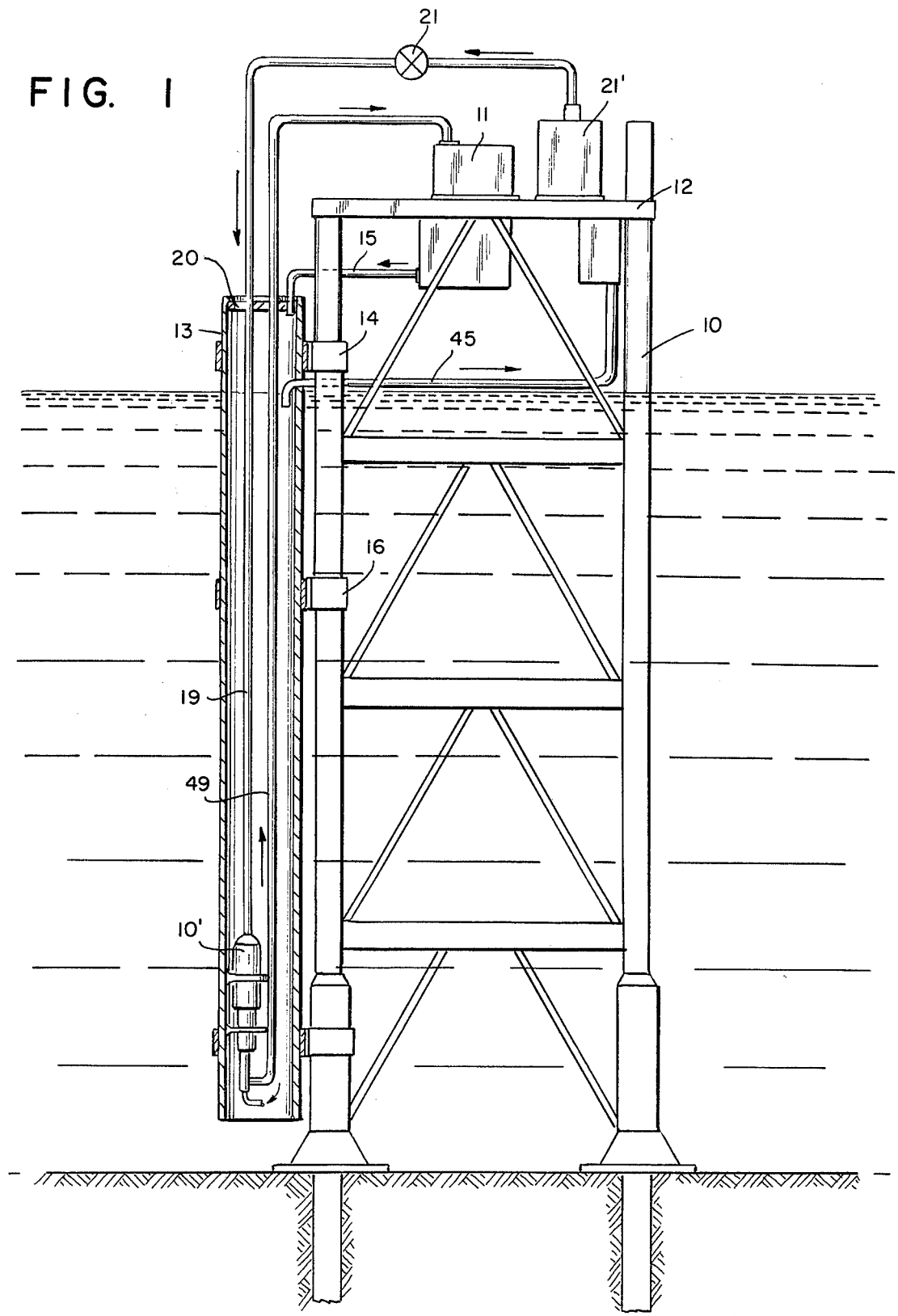
FIG. 1 illustrates an embodiment of the instant disposal pile depending from a marine structure.

The accompanying drawings illustrate an installation of the type contemplated wherein a water sampling apparatus contained within a partially submerged pool holding caisson, is communicated with testing apparatus at the water's surface.

While not specifically shown in detail, the above surface portion of the instant apparatus is carried on an offshore or marine structure 10. Said structure can be either buoyantly maintained at the water's surface, or fixedly positioned as shown, to the ocean floor. In either instance sample testing apparatus 10' will be positioned on an elevated deck 12.

Normally the equipment for initially treating the production from a well will include primarily a separator of some form capable of separating crude oil from the water and gas which normally flow from the well.

A caisson 13 or elongated pile is vertically positioned on, and adjacent to the offshore structure 10. Said caisson receives in its upper end the flow of used and treated water which results from the producing operation. This untreated water is deposited into the caisson upper end from a discharge pipe 15. The caisson or pile comprises in essence an elongated member such as a cylindrical steel tube having the lower end open and the side walls maintained water tight, with an upper closure 20 vented to the atmosphere. A series of vertically spaced brackets 14 and 16, fastens the caisson to the structure 10.

The caisson 13 lower end is positioned above the floor of the ocean to permit free egress of water which gravitates downwardly. The lighter than water residue which rises to the caisson upper end is periodically removed through conduit 25, to be further treated or disposed of.

Figure 2:
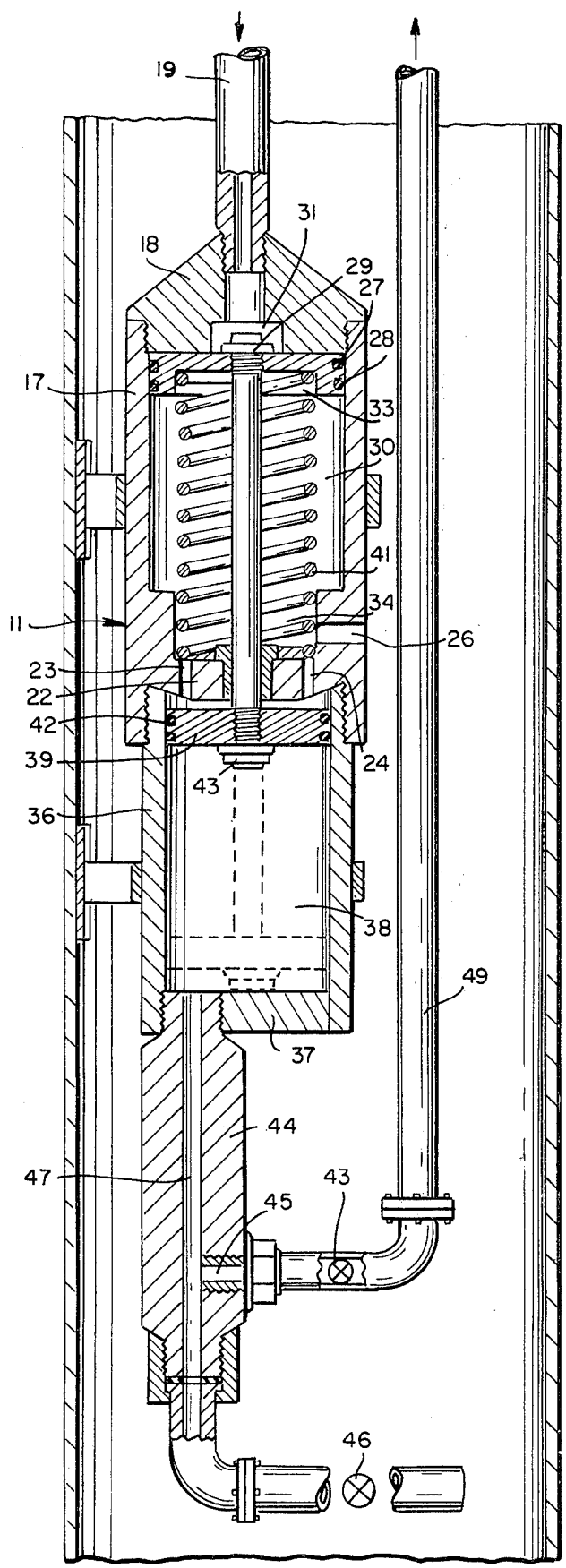
FIG. 2 illustrates in cross section the water pumping apparatus of FIG. 1.

Referring to FIG. 2, the water sampling means 11 includes an elongated casing 17 disposed in a substantially upright position and having a closure cap 18 fixed to the upper end. Cap 18 threadably receives an elongated conduit 19 which extends to the water's surface, and thence to flow control means 21 such as a manually or automatically actuated valve means. The latter is in turn attached to a source of pressurized gas 21 which as mentioned, can be compressed gas, preferably a source obtained directly from the processing equipment on platform 10.

Casing 17 is provided at the lower end with an intermediate transverse panel 22 which is fixedly retained therein or which can be integral with the adjacent cylinder wall. Said panel 22 embodies passage means, including at least one and preferably a plurality of short connecting passages 23 and 24 which traverse the panel to permit liquid flow therethrough.

A vent opening 26 traverses the casing 17 wall at the lower end thereof adjacent to where a first piston 27 will terminate its downward travel.

Piston 27 includes a plurality of peripheral seal rings 28 and is slidably received within cylindrical casing 17 to define a chamber 30. Piston 27 embodies a central opening adapted to receive the end of elongated piston rod 35. The latter receives a nut 29 fastened to its upper end to position rod 35 firmly on the piston. A cavity 31 formed within cap 18 immediately above piston 27 receives nut 29 when the piston is urged into its upward position.

Thus, when pressurized gas from source 10' is forced into cavity 31 by opening of control valve 21, piston 27 will be urged downward into chamber 30 against the biasing pressure of coil spring 41. Said spring is disposed longitudinally of piston rod 35 and is positioned within a cavity 33 defined by an upstanding rim within the piston's lower face, and by a corresponding cavity 34 formed in the walls of panel 22.

A second casing 36 is threadably fixed to and depends from the end of first casing 17. A lower transverse end wall 37 defines in part collecting chamber 38. Chamber 38 includes in essence a cylindrical inner wall which slidably guides a second piston 39 therein. A pair of peripherally arranged seal rings 42 insure the fluid tight integrity of the collecting chamber into which piston 39 is reciprocally moved. Piston 39 includes a fastening nut 43 at the lower side thereof to position said piston onto the lower end of piston rod 35.

Operationally, both pistons 27 and 39 will move simultaneously through the respective chambers 30 and 38 as gas is supplied to the chamber 30. Thus, the pressurizing of the power piston 27 causes the lower piston 39 to discharge fluid contained in the receiving or collecting chamber 38.

The passage of water into and from collecting chamber 38 is effectuated by an elongated manifold 44 having a connecting end. The latter threadably engages the lower casing wall 37, and is sealably positioned therein.

Manifold 44 includes an inlet at the lower end having a check valve 46 positioned to permit the entry of water through elongated passage 47 and thence into the collecting chamber 38. This latter movement is achieved initially by piston 39 being at the lower end of collecting chamber 38, and thereafter as gas pressure is relieved against the upper piston 27, lower piston 39 will be urged upward by spring 41 to permit the ingestion of water into the collecting chamber.

Likewise, on the discharge stroke, downward movement of piston 39 in response to gas pressure against piston 27, will urge the collected water downward through the elongated passage 47 where its passage will be determined by closure of the lower check valve 46 and the opening of the second check valve 48. The latter is communicated with said elongated passage 47 by port 45, and by elongated discharge conduit 49.

The upstream side of said check valve 48 is communicated through elongated conduit 49 to the water's surface and thence to the sample receiving and testing apparatus 11. At the latter, water can then be collected and suitably labeled for analysis.

Operationally, during any petroleum processing operation on deck 12 of offshore structure 10, residual water normally containing some petroleum based ingredient which will float to the water's surface, is introduced to the caisson 13 through discharge pipe 15. This water will tend to settle into the caisson, the lighter, water polluting components will then float to the caisson upper end equivalent to the position of the water external to the casing 13.

The remaining, pollutant free water will gravitate to the bottom of casing 13 where it will be communicated through the lower opening with the surrounding water.

To achieve the herein noted water sampling purposes, water samples are drawn from the bottom end of caisson 13 immediately prior to its being discharged. This is done by periodic manipulation of the gas control valve 21 at the platform deck 12 as to urge first piston 27 downwardly into its lower position in chamber 30. Thereafter by releasing the gas pressure in chamber 30, piston 27 will return upwardly to ingest a quantity of the pollutant free water. The sampling procedure can as mentioned be carried out either manually as needed, or on a continuous cycle basis. In either event, sampling is achieved through the regulation of flow control valve 21.

Discharge of sample water from collecting chamber 38 follows by again applying gas pressure to the upper face of the piston 27 which in turn urges lower piston 39 through collecting chamber 38.

Other modifications and variations of the invention as hereinbefore set forth can be made without departing from the spirit and scope thereof, and therefore, only such limitations should be imposed as are indicated in the appended claims.

I claim:

1. The combination with a marine structure positioned at an offshore body of water and being communicated with a source of process gas resulting from a hydrocarbon producing operation, which operation further yields a supply of an immiscible dispersion liquid comprising waste water and hydrocarbon liquid, of an upstanding elongated disposal caisson communicated with said immiscible dispersion liquid supply for effecting a gravity separation of the water component thereof from the hydrocarbon liquid, and a discharge port positioned at the disposal caisson lower end, a pump positioned at the caisson lower end and including means forming coaxially arranged power chamber and collecting chamber, a piston slidably received in reciprocal movement between advanced and retracted positions in each of said respective power and collecting chambers, and being connected by a common piston rod, means communicating said power chamber with a source of a pressurized gas whereby to displace piston in said power chamber when an amount of said pressurized gas is introduced thereto, a passaged panel means disposed intermediate the respective power and collecting chambers to slidably register said piston rod therein, and to communicate the respective chambers one with the other, biasing means engaging at least one of said pistons to urge the same into a retracted position at one end of the respective power and collecting chambers, venting means communicating the power chamber with said immiscible dispersion liquid to permit a flow of the said liquid through the respective chambers and through said passaged panel during reciprocal movement of the piston through the respective chambers, flow control means including, a first valved passage communicating the collecting chamber with liquid at the caisson lower end and being operable to permit a stream of said liquid to be drawn into said collecting chamber when the piston is moved to the retracted position, and a second valved passage being operable to direct said stream of liquid from said collecting chamber during the piston discharge stroke, and conduit means communicated with said second valved passage and extending to the water's surface whereby said stream of liquid can be delivered to the latter.

2. In an apparatus as defined in claim 1 including biasing means disposed within said power chamber and engaging said piston therein for urging the piston through said collecting chamber to draw said stream of liquid thereinto.

3. In an apparatus as defined in claim 2, wherein said biasing means includes a compression spring.

4. In an apparatus as defined in claim 1, wherein said passaged panel intermediate said power chamber and said collecting chamber, includes at least one transverse passage formed in said passaged panel providing communication with the respective chambers.

* * * * *